United States Patent [19]

Ikeda et al.

[11] 3,933,770

[45] Jan. 20, 1976

[54] METHOD OF PREPARING TRANSITION METAL COMPLEX CATALYSTS

[75] Inventors: Sakuji Ikeda; Atsumu Ozaki; Makoto Okawara, all of Tokyo; Tsutomu Mizoroki, Yokohama; Masahiro Uchino, Tokyo; Hideki Shirakawa, Yokohama; Noboru Kawata, Kawasaki, all of Japan

[73] Assignee: Tokyo Institute of Technology, Tokyo, Japan

[22] Filed: Mar. 20, 1974

[21] Appl. No.: 452,839

[30] Foreign Application Priority Data

Sept. 13, 1973  Japan.............................. 48-103678

[52] U.S. Cl....... 260/87.5 R; 260/80 C; 260/88.2 S; 260/89.1; 260/89.5 A; 260/93.5 A; 260/683.15 D; 252/431 R

[51] Int. Cl.$^2$..... C08F 8/30; C08F 8/40; C08F 8/42
[58] Field of Search......... 260/93.5 A, 88.2 S, 96 R, 260/87.5 R, 91.5; 450/614, 619

[56] References Cited
UNITED STATES PATENTS
3,342,755  9/1967  Calmon et al. ...................... 260/2.2

*Primary Examiner*—Stanford M. Levin
*Attorney, Agent, or Firm*—Burgess Ryan and Wayne

[57] ABSTRACT

There is provided a method of preparing transition metal complex catalysts combined with organic high polymers.

2 Claims, No Drawings

METHOD OF PREPARING TRANSITION METAL COMPLEX CATALYSTS

BACKGROUND OF THE INVENTION

There have been proposed transition metal complex catalysts for use in the polymerization of alkene and alkyne. Such catalysts are, for example, complexes having the following formulas:

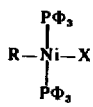  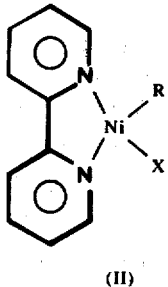

(I)  (II)

wherein $\Phi$ is phenyl group, R is an alkyl group of 1 to 3 carbon atoms or an aryl group such as phenyl, tolyl, xylyl or naphthyl, and X is Cl, Br or I.

Such complex catalysts may be prepared by the reaction of tetrakis(triphenylphosphine(nickel or α-dipyridyl(dialkyl)nickel with halogenated compound as follows:

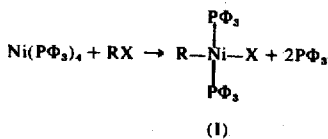

(I)

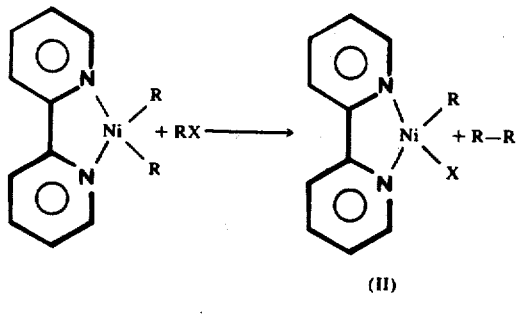

(II)

The complex catalysts having the formulas (I) and (II) are objectionable in that they are thermally decomposable. Accordingly, these catalysts cannot be recovered after they have been used as a catalyst in the polymerization, i.e. they are very difficult to use repeatedly.

It is, therefore, an object of the present invention to provide thermally stable catalysts for use in the polymerization of alkene and alkyne.

SUMMARY OF THE INVENTION

The present invention relates to a method of preparing transition metal complex catalysts combined with organic high polymers. Said catalysts have, for example, the following structural formula:

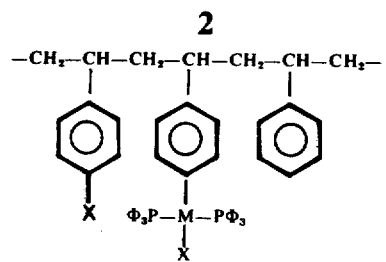

M: Ni, Pd or Pt $\Phi$: $C_6H_5$

X: Cl, Br or Y

Nomenclatures and chemical formulas or structural formulas of the compounds used in this application are as follows:

Halogenated polystyrene

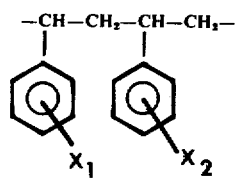

$X_1$: Cl, Br or I $X_2$: H, Cl, Br or I

Halogenated styrene-divinylbenzene copolymer

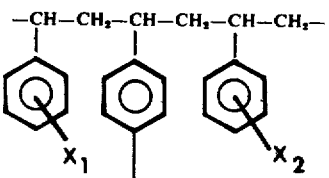

$X_1$, $X_3$: Cl, Br or I $X_2$, $X_4$: H, Cl, Br or I

Tetrakis(triphenylphosphine)nickel
$Ni(P\Phi_3)_4$  $\Phi$: $C_6H_5$
Tetrakis(triphenylphosphine)palladium
$Pd(P\Phi_3)_4$
Tetrakis(triphenylphosphine)platinum
$Pt(P\Phi_3)_4$
Diethyl(dipyridyl)nickel

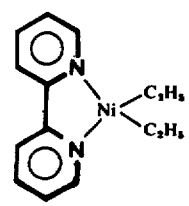

Bis(triphenylphosphine)phenyl(bromo)nickel

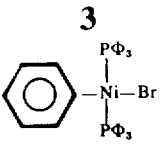

The catalysts of the present invention may be prepared in the following manner:

1. A halogenated high polymer is mixed with a transition metal complex in an organic solvent.
2. The mixture is vigorously agitated and then allowed to stand to produce precipitate. This precipitate is filtered and then washed with an organic solvent to obtain a transition metal complex catalyst combined with organic high polymer of the present invention.

Said halogenated high polymer includes halogenated polystyrene and halogenated styrene-divinylbenzene copolymer.

Said transition metal complex includes complexes of transition metals which are in the low oxidation state, such as tetrakis(triphenylphosphine)nickel, tetrakis(triphenylphosphine)palladium, tetrakis(triphenylphosphine)platinum and diethyl(dipyridyl)nickel.

As an organic solvent, benzene, toluene or n-hexane may preferably be used.

The catalysts thus prepared have advantages as follows:

1. They are thermally stable.
2. They aare insoluble in common organic solvents such as benzene, toluene, n-hexane, methylene chloride, chlorobenzene and the like.
3. They can easily be separated from liquid products and repeatedly used.

The invention is illustrated by the following examples.

EXAMPLE 1.

4.5 g of brominated polystyrene (average degree of polymerization 1,100, bromination in the para-position of phenyl rings of polystyrene 80 percent was dissolved in 150 ml of toluene, and to this solution was added a solution of tetrakis(triphenylphosphine)nickel (which has been prepared from bis(acetylacetonato)nickel 5g, triphenylphosphine 20 g and diethyl(monethoxy)aluminum 8ml) in 100 ml of toluene. After this mixture was vigorously agitated for about one hour, it was allowed to stand for about 12 hours to give brownish precipitate. Supernatant liquid was removed and precipitate was washed five times with n-hexane to obtain 6.5g of nickel complex catalyst combined with brominated polystyrene having the following structural formula:

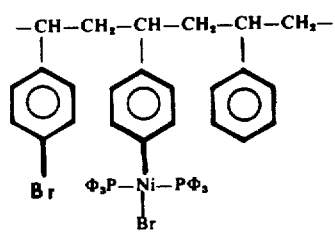

In this complex catalyst, nickel content was 0.495 mmol/g.

0.1g of the nickel complex catalyst prepared above was suspended in 10 ml of n-hexane and to this suspension was added 0.8 mmol of ethyl ether-boron trifluoride (1/1). Ethylene gas was introduced into the mixture at 0°C and then subjected to the reaction at a pressure of 1 atmosphere. Ethylene gas was absorbed at a rate of 41.4 ml/min to produce selectively butene by dimerization of ethylene.

The nickel complex catalyst could easily be recovered by removing butene and n-hexane after the reaction. Dimerization of ethylene was carried out twice by using the recovered nickel complex catalyst under the same condition as above. In these dimerizations, ethylene was absorbed at a rate of 50.3 ml/min and 56.3 ml/min, respectively.

For the purpose of comparison, dimerization of ethylene was carried out by using a solution of bis(triphenylphosphine)phenyl(bromo)nickel (0.049 mmol) in methylene chloride (10 ml) under the same condition as above. In this dimerization, ethylene was absorbed at a rate of 39.6 ml/min.

EXAMPLE 2

5.1g of nickel complex catalyst combined with iodinated polystyrene was obtained by repeating the same procedure as that of Example 1 except that 4.5g of iodinated polystyrene (average degree of polymerization 1100, iodination 89 percent was used instead of 4.5g of brominated polystyrene. In this complex catalyst, nickel content was 0.304 mmol/g.

EXAMPLE 3

160mg of chlorinated polystyrene (average degree of polymerization 700, chlorination 100 percent and 140 mg of diethyl(dipyridyl)nickel were added to 40 ml of toluene and this mixture was agitated at 50°C for 15 hours to give reddish precipitate. The precipitate was filtered, washed with toluene and dried to obtain nickel complex catalyst of the following formula:

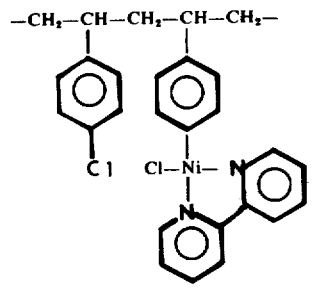

This process was carried out in an atmosphere of nitrogen.

The nickel complex catalyst thus obtained can suitably be used as a catalyst for polymerization of methyl methacrylate or vinyl acetate and as a catalyst for oligomerization of alkene such as ethylene or propylene in the presence of diethylaluminium chloride.

EXAMPLE 4

3.0g of iodinated polystyrene (average degree of polymerization 1100, iodination 96 percent was dissolved in 100 ml of benzene and to this solution was added a solution of 7g of tetrakis(triphenylphosphine)palladium in 100 ml of benzene. After this mixture was vigorously agitated for about one hour, it was allowed to stand for about 12 hours to give light yellowish precipitate. After an supernatant liquid was removed and the precipitate was washed twice with benzene and once with n-hexane, the precipitate was dried under reduced pressure to obtain 3.5g of palladium complex catalyst combined with iodinated polystyrene. In this complex, palladium content was 0.45 mmol/g.

EXAMPLE 5

3.0g of iodinated polystyrene (average degree of polymerization 1100, iodination 96.4 percent) was dissolved in 150 ml of benzene and to this solution was added a solution of 5g of tetrakis(triphenylphospine) platinum in 100 ml of benzene. After this mixture was vigorously agitated at a temperature of 70°C to 6 80°C for about 6 hours, it was allowed to stand for about 12 hours to give pale yellowish precipitate. The precipitate was filtered and washed with benzene (thrice) and with n-hexane (twice), and then dried under reduced pressure to obtain 3.6g of platinum complex catalyst combined with iodinated polystyrene. This platinum complex catalyst is insoluble in common organic solvents and stable in the air.

EXAMPLE 6

0.5g of p-chlorostyrene-divinylbenzene copolymer was suspended in 100 ml of toluene and to this suspension was added 0.28g of diethyl(dipyridyl)nickel. This mixture was kept, with stirring, at a temperature of about 50°C for 24 hours. After the mixture was allowed to stand, the supernatant liquid was removed and the precipitate was washed with toulene thrice to give 0.51g of nickel complex catalyst combined with styrene-divinylbenzene copolymer of the following formula:

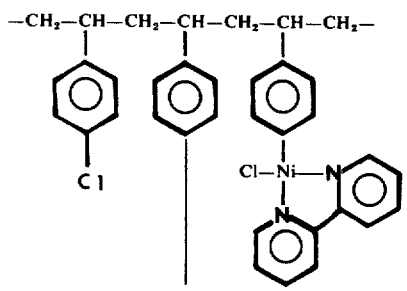

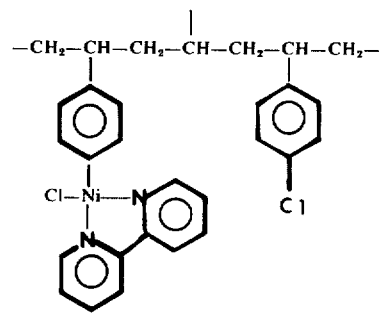

In this complex, nickel content was 0.21 mmol/g.

In the above Examples, triphenylphosphine ($P\Phi_3\Phi$: phenyl group) was used. However, other tertiary phosphines may be used instead of triphenylphospine. Such tertiary phosphines are those of the following formulas:

$P(C_2H_5)_3$, $PC_2H_5(C_6H_5)_2$, $PCl(C_6H_5)_2$, $P(OC_6H_5)_3$, $P(C_2H_5)_2C_6H_5$.

We claim:

1. A method for preparing transition metal complex catalysts combined with organic high polymers, comprising mixing a halogenated high polymer selected from the group consisting of chlorinated, brominated and iodinated polystyrene and chlorinated, brominated and iodinated styrene-divinylbenzene copolymer with a complex of transition metal selected from the group consisting of nickel, palladium and platinum in an organic solvent, said transition metal being in a low oxidation state.

2. A method according to claim 1 said transition metal complex is one selected from the group consisting of tetrakis(triphenylphosphine)nickel, tetrakis(triphenylphosphine)palladium, tetrakis(triphenylphosphine)platinum and diethyl(dipyridyl)nickel.

* * * * *